United States Patent
McDowell

(10) Patent No.: US 12,029,877 B1
(45) Date of Patent: Jul. 9, 2024

(54) MEDICAL LINE HOLDER DEVICE

(71) Applicant: Arnolia Thompson McDowell, Houston, TX (US)

(72) Inventor: Arnolia Thompson McDowell, Houston, TX (US)

( * ) Notice: Subject to any disclaimer, the term of this patent is extended or adjusted under 35 U.S.C. 154(b) by 0 days.

(21) Appl. No.: 18/397,486

(22) Filed: Dec. 27, 2023

Related U.S. Application Data

(60) Provisional application No. 63/504,937, filed on May 30, 2023.

(51) Int. Cl.
| | |
|---|---|
| *A61M 5/14* | (2006.01) |
| *A61G 7/05* | (2006.01) |
| *A61H 3/00* | (2006.01) |

(52) U.S. Cl.
CPC ............. *A61M 5/1418* (2013.01); *A61G 7/05* (2013.01); *A61M 5/1415* (2013.01); *A61H 2003/002* (2013.01); *A61M 2205/60* (2013.01)

(58) Field of Classification Search
CPC .............. A61M 5/1418; A61M 5/1415; A61M 2205/60; A61G 7/05; A61H 2003/002
USPC ........................................................ 604/174
See application file for complete search history.

(56) References Cited

U.S. PATENT DOCUMENTS

| | | | |
|---|---|---|---|
| 3,726,280 A | 4/1973 | Lacount | |
| 4,639,980 A | 2/1987 | Peterson | |
| 5,702,039 A * | 12/1997 | Olaiz | B62B 3/1456 24/3.13 |
| 8,679,065 B2 | 3/2014 | Schuman et al. | |

FOREIGN PATENT DOCUMENTS

| | | |
|---|---|---|
| EP | 2705872 A1 | 8/2016 |
| EP | 2253350 B1 | 9/2016 |

\* cited by examiner

*Primary Examiner* — Phillip A Gray

(57) ABSTRACT

The medical line holder device is intended to provide users with a holder that can protect a patient's medical lines when moving around or during rest. To accomplish this, the device includes a main support strip with hook and loop fasteners at the top and the bottom. The fasteners at the top allow the top of the support to be attached to a walker or IV pole and those at the bottom securely hold large medical tubes. Further, two small hook and loop strips in the middle are provided for holding small medical tubes. Thus, the device can safely secure multiple IV lines, feeding tube lines etc. in small closures while also securing larger multiple chest tube lines during mobility or at rest. This protects patient lines from unsafe occurrences or becoming entangled in the IV pole during mobility or while being handled for set up by bedside staff.

11 Claims, 6 Drawing Sheets

MEDICAL LINE HOLDER DEVICE

FIELD OF THE INVENTION

The present invention generally relates to a medical line/tube holder device. More specifically, the present invention is intended to provide a holder to protect acute patient's medical lines from all types of tangling and also protects from floor contact when moving around the areas.

BACKGROUND OF THE INVENTION

It is common knowledge that household items, such as window blind cords, are potential hazards. However, many people may not expect that medical devices may pose similar risks because of medical line entanglement (MLE) or dislodging. Lines and tubes come in a variety of shapes and sizes, and for varied purposes. Peripheral IVs (intravenous), intraosseous catheter, midline catheter, etc. are some examples. Patient tube/line management has significant implications on ICU staff and all hospital staff workload during early mobility. Safely securing multiple IV lines, feeding tube etc. while also securing larger chest tube lines during mobility or at rest is a challenge for hospital staff and patients as well as caregivers. Further, lines that extend to the floor or go around IV pole may cause dislodgement or become entangled during mobility or while being handled by bedside staff. Thus, there is a need for healthcare facilities for managing risks of MLE and reducing the risk of dislodgement.

It is an objective of the present invention to provide a holder that can protect a patient's medical lines when moving around or during rest. To that end, the present invention can safely secure multiple IV lines, feeding tube lines, wound vac lines etc. in small closures while also securing larger multiple chest tube lines during mobility or at rest in large enclosures. The present invention also protects patient lines from unsafe occurrence/dislodgement that can be experienced with lines going to the floor or becoming entangled in the IV pole during mobility or while being handled for set up by bedside staff. Securing the lines also brings added security for patients and decreases the patient's anxiety during mobility. Further, the present invention can be transferred from the IV pole to a rolling walker during mobility as needed with the patient and staff is able to focus on movement and feel secure about the fact that the medical lines are safely contained. Thus, the present invention is a protective addition that allows the patient to move around freely with a reduced risk of line entanglement and without stepping on the lines or getting the lines tangled up.

SUMMARY

The present invention is a medical line holder device. It is an objective of the present invention to provide a holder that can protect a patient's medical lines when moving around or during rest. To accomplish this, the present invention comprises a main support strip with hook and loop fasteners at the top and the bottom. The fasteners allow the top of the support to be attached to a walker or IV pole. Further, the hook and loop fasteners at the bottom help securely hold large medical tubes such as chest tubes, for example. Additionally, two small hook and loop strips in the middle that fold over are provided for holding small medical tubes. In other words, the present invention can safely secure multiple IV lines, feeding tube lines etc. in small closures while also securing larger multiple chest tube lines during mobility or at rest. This protects patient lines from unsafe occurrence/dislodgement that can be experienced with lines going to the floor or becoming entangled in the IV pole during mobility or while being handled for set up by bedside staff. Securing the lines also brings added security for patients and decreases the patient's anxiety during mobility. Furthermore, the present invention may be transferred from the IV pole to a rolling walker during mobility as needed with the patient and staff will be able to focus on movement and feel secure that the medical lines are safely contained. Thus, the present invention is a protective addition that allows the patient to move around freely without stepping on the lines or getting the lines tangled up or trying to manage the lines themselves manually.

DETAIL DESCRIPTIONS OF THE INVENTION

All illustrations of the drawings are for the purpose of describing selected versions of the present invention and are not intended to limit the scope of the present invention.

In reference to FIG. 1 through FIG. 6, the present invention is a medical line holding device.

Figure 1:
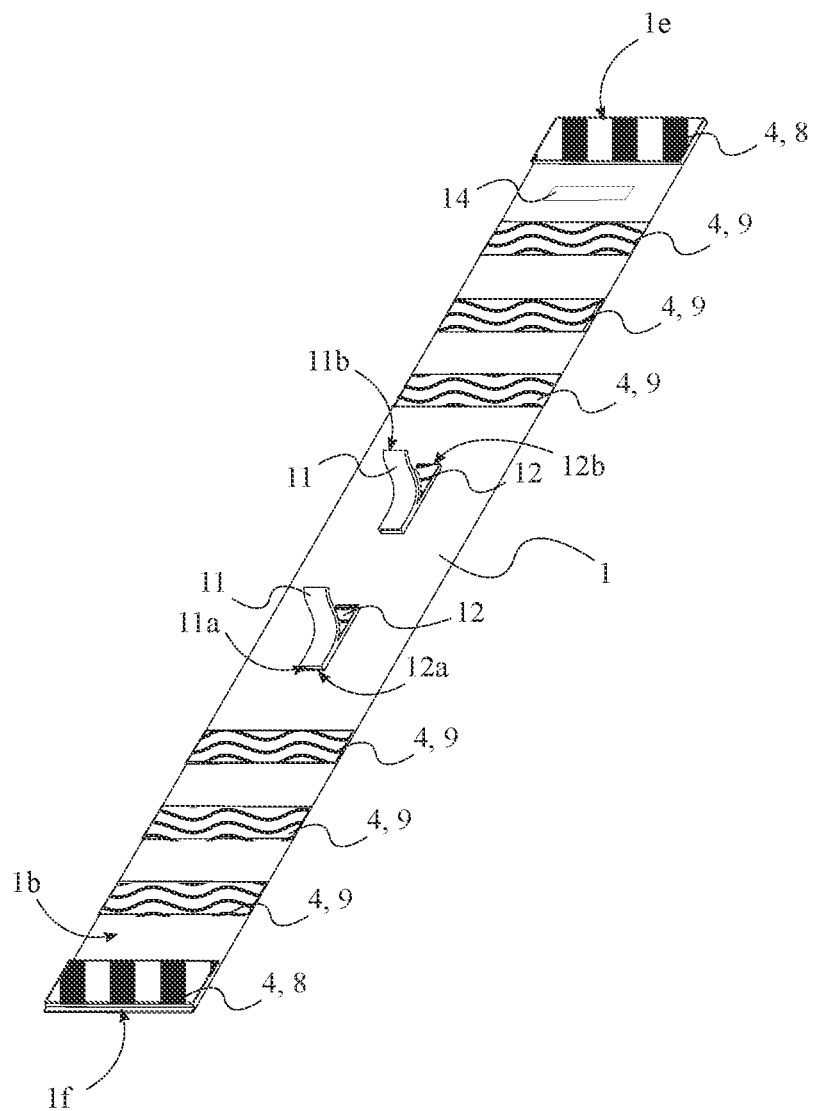
FIG. 1 is a top-front-left perspective view of the present invention.
Figure 2:
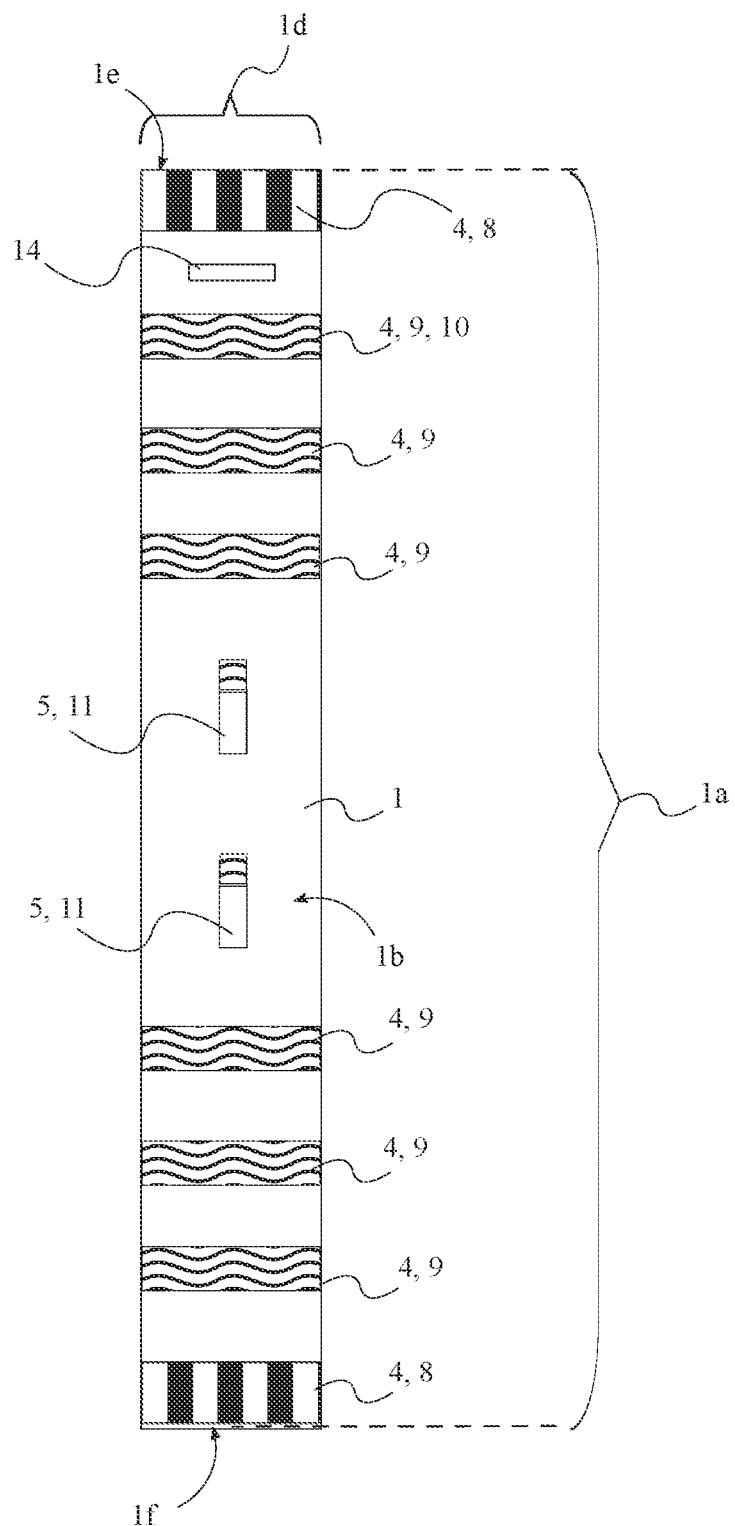
FIG. 2 is a front elevational view of the present invention.
Figure 3:
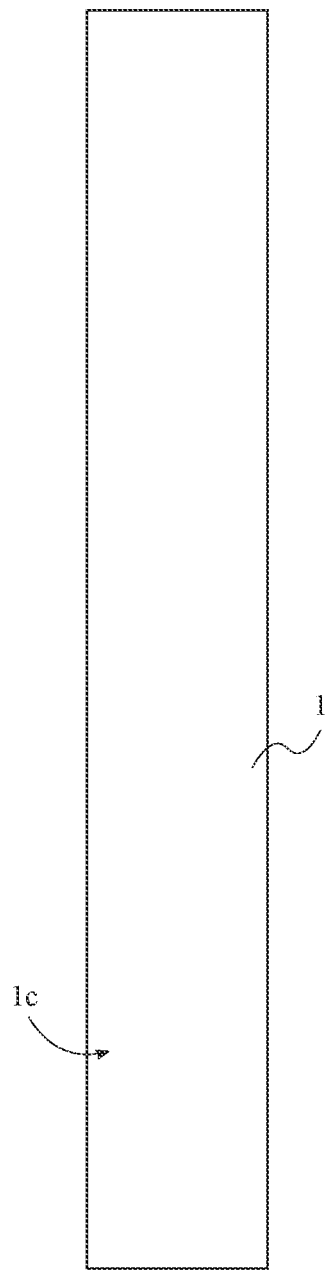
FIG. 3 is a rear elevational view of the present invention.
Figure 4:
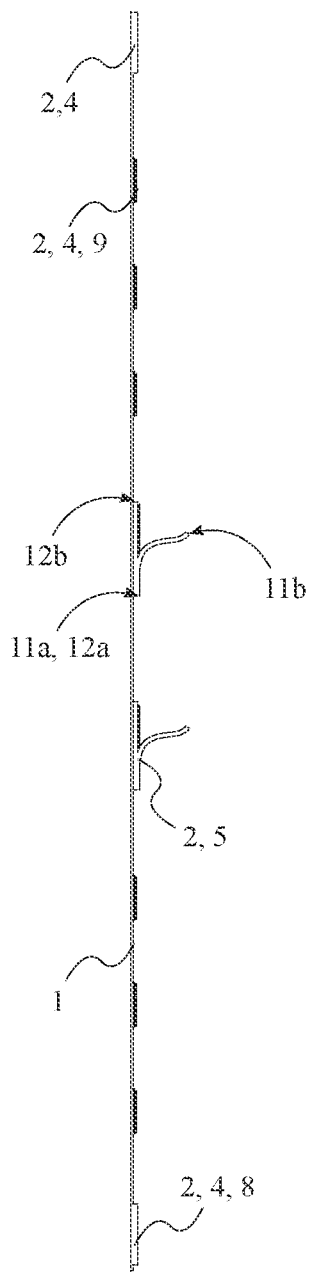
FIG. 4 is a side elevational view of the present invention.
Figure 5:
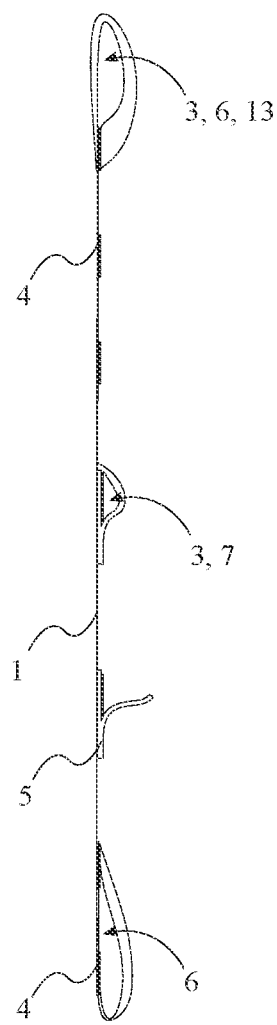
FIG. 5 is a side perspective view of the present invention, wherein loops of different sizes are made with the plurality of fasteners.

The following description is in reference to FIG. 1 through FIG. 6. According to a preferred embodiment, the present invention comprises a support fabric 1, a plurality of fasteners 2, and a plurality of loops 3. Preferably, the support fabric 1 is a rectangular piece of fabric that is made up of a six and one forth (61/4) inch wide nylon strip that is 39 inches long. However, the support fabric 1 may comprise any other material, size, components, arrangement of components, etc. that are known to one of ordinary skill in the art, as long as the intents of the present invention are not altered. According to the preferred embodiment, the plurality of fasteners 2 is distributed along a length 1a of the support fabric 1 and laterally connected onto a first surface 1b of the support fabric 1. A second surface 1c of the support fabric 1 that is positioned opposite to the first surface 1b across the support fabric 1, is left free without any fastening elements. In other words, and as seen in FIG. 2 and FIG. 3, the first surface 1b constitutes the front surface of the present invention and the second surface 1c constitutes a rear surface of the present invention. Preferably, the plurality of fasteners 2 comprises hook and loop fasteners that are glued and/or stitched to the support fabric 1. However, the plurality of fasteners 2 may comprise any other size, shape, fastening technology, etc. that are known to one of ordinary skill in the art, as long as the intents of the present invention are fulfilled. Further, the plurality of fasteners 2 comprises a first set of fasteners 4 and a second set of fasteners 5. Preferably, the support fabric 1 may be rolled or folded at various points and engaged with the plurality of fasteners 2 to create different loops that can securely hold the medical lines. In the preferred embodiment, the second set of fasteners 5 is positioned between the first set of fasteners 4. In other words, the larger first set of fasteners 4 is positioned on opposing sides of the smaller second set of fasteners 5, which are positioned towards the middle of the support fabric 1. Preferably, the first set of fasteners 4 are used for creating bigger loops that can securely hold larger tubes and lines such as chest tubes, head rail, IV pole etc., while the second set of fasteners 5 in the middle may be used for creating smaller loops that can hold smaller tubes such as IV lines, feeding tubes, etc. To that end, the plurality of loops 3 comprises a first set of loops 6 and a second set of loops 7. As seen in FIG. 5, the first set of loops 6 is bigger than the second set of loops 7.

Figure 6:
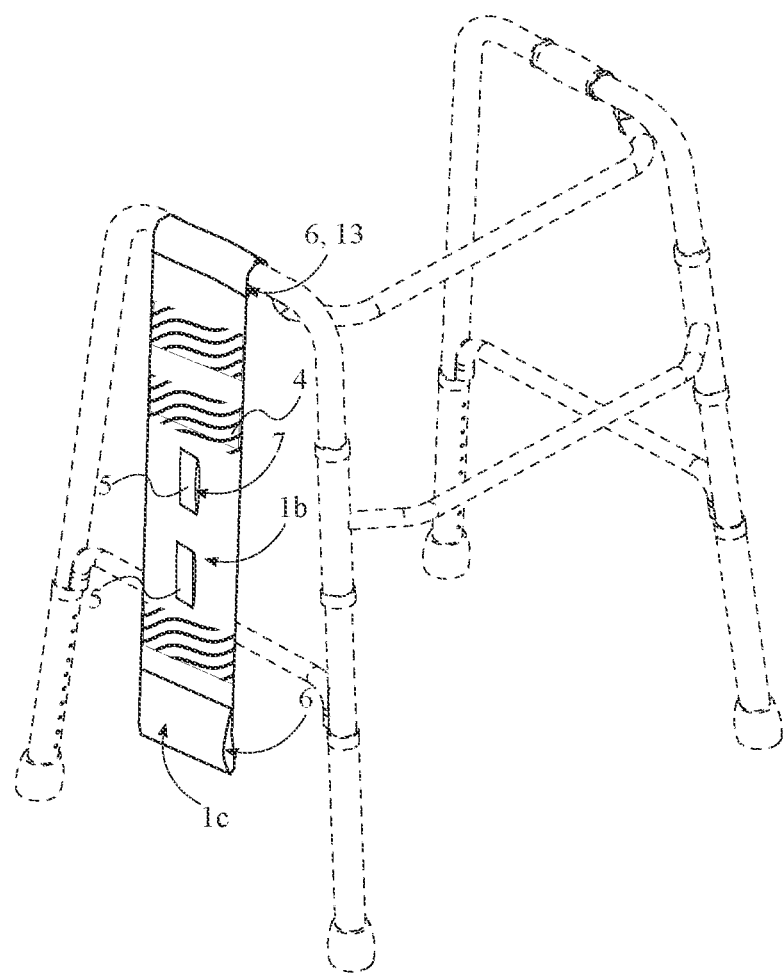
FIG. 6 is a perspective view of the present invention, wherein the present invention is hung from the handle of a walker.

As specified above, the first set of fasteners 4 is detachably engaged to create the first set of loops 6, and the second set of fasteners 5 is detachably engaged to create the second set of loops 7. In the preferred embodiment, the first set of loops 6 is created by rolling or bending of the support fabric 1 followed by engagement of the first set of fasteners 4. However, different types of fasteners may comprise different modes of operation for engagement. As seen in FIG. 6, the first set of loops 6 is oriented normally to the length 1a and oriented parallel to a width 1d of the support fabric 1.

A more detailed description of the present invention follows.

According to the preferred embodiment, the first set of fasteners 4 comprises a plurality of connector ends 8 and a plurality of connection ends 9. Preferably, the plurality of connector ends 8 constitutes the smooth side of a hook and loop fastener, which is the hook side. Similarly, the plurality of connection ends 9 constitutes the rough side of a hook and loop fastener, which is the loop side. Preferably, the plurality of connector ends 8 is positioned adjacent to terminal ends of the support fabric 1. In other words, in the preferred embodiment, the top end and the bottom end of the support fabric 1 has a 6 and ¼ inch long strip of smooth hook part (of a hook and loop fastener) going across the top edge or aligned along the width 1d of the support fabric 1. As seen in FIG. 1, the plurality of connection ends 9 is positioned between the plurality of connector ends 8. In other words, every 2 inches below the top hook segment, there are three 6 and ¼ inch long strips of loops (of a hook and loop fastener) each with 2 inches in between. Further, there are three 6 and ¼ inch long strips of loops each 2 inches apart coming up from the bottom hook segment as well. Thus, as seen in FIG. 1 and FIG. 2, the plurality of connector ends 8 and the plurality of connection ends 9 is distributed along the length 1a of the support fabric 1, and each of the plurality of connector ends 8 and the plurality of connection ends 9 is laterally offset from each other. However, it should be noted that the plurality of connector ends 8 and the plurality of connection ends 9 may comprise any other size, shape, separation, orientation, location, etc. that are known to one of ordinary skill in the art, as long as the intents of the present invention are not altered.

According to the preferred embodiment, each of the plurality of connector ends 8 is detachably engaged with a corresponding connection end 10 to form the first set of loops 6, wherein the corresponding connection end 10 is from the plurality of connector ends 8. In other words, when a connector end from the plurality of connector ends 8 is connected to or fastened with a connection end, a loop or space big enough to securely wrap around railings, IV pole etc. is formed, and these loops constitute the first set of loops 6. More specifically, diameters or spaces between the first set of loops are large enough to be attached around at least one of a walker, a bed railing, and IV (intravenous) pole.

Continuing with the preferred embodiment, the second set of fasteners 5 comprises a plurality of connector segments 11 and a plurality of connection segments 12. Preferably, the plurality of connector segments 11 constitutes hook elements and the plurality of connection segments 12 constitutes loop elements of smaller 1 and ½ inches long hook and loop fasteners. In the preferred embodiment, one end of each of the plurality of connection segments 12 is permanently attached to one end of the plurality of connector segments 11. In other words, a first end 11a of the plurality of connector segments 11 is permanently attached to a first end 12a of the plurality of connection segments 12. As seen in FIG. 1 and FIG. 2, the small hook and loop fastener strips in the middle of the support fabric 1, fold over for small medical tubes. To that end, each of the plurality of connector segments 11 comprises a second end 11b, wherein the second end 11b is positioned opposite to the first end 11a across the plurality of connector segments 11. Further, each of the plurality of connection segments 12 comprises a second end 12b, wherein the second end 12b is positioned opposite to the first end 12a across the plurality of connection segments 12. This enables the user to just place the smaller tubes in between the open parts of the connection segments 12 and quickly fasten/close the open end of the connector segment 11 to create a strong hold. In other words, the second end 11b of the plurality of connector segments 11 is detachably engaged to the second end 12b of the plurality of connection segments 12 to form the second set of loops 7. Preferably, diameters or spaces between the second set of loops 7 is small enough to securely hold at least one of catheter line and IV line.

As seen in FIG. 1 and FIG. 2, the support fabric 1 comprises a third end 1e and a fourth end 1f, and the third end 1e is positioned opposite to the fourth end 1f across the length 1a of the support fabric 1. Preferably, the third end 1e constitutes a top end of the support fabric 1 and the fourth end 1f constitutes a bottom end of the support fabric 1. Further, a support loop 13 from the first set of loops is positioned adjacent to the third end 1e. In other words, the support loop 13 constitutes a loop from the first set of loops 6 that is usually used to hang the present invention from a support structure. More specifically, the support loop 13 is the loop created by the connector end and the connection end that are adjacent to each other and adjacent to the third end 1e of the support fabric 1. Thus, as seen in FIG. 6, the support loop 13 is wrapped around at least one of a walker, an IV pole, and a bed railing.

It is an aim of the present invention for users to find out the top end and bottom end of the support fabric or orientation of the support fabric so as to easily attach and detach the support fabric around various support structures and carefully hold the medical lines in necessary loops. To accomplish this, the present invention comprises an instructional tag 14, wherein the instructional tag 14 is affixed adjacent to the third end 1e. Further, the instructional tag 14 indicates an orientation of the support fabric 1. Preferably, the instructional tag 14 is a label sewn onto the support fabric 1 adjacent to the top end or third end 1e. However, the instructional tag 14 may comprise any other material, shape, size, fastening technique etc. that are known to one of ordinary skill in the art, as long as intents of the present invention are not altered.

Although the invention has been explained in relation to its preferred embodiment, it is to be understood that many other possible modifications and variations can be made without departing from the spirit and scope of the invention as hereinafter claimed:

1. A medical tubes holder device comprising:
a support fabric;
a plurality of fasteners;
a plurality of loops;
the plurality of fasteners comprising a first set of fasteners and a second set of fasteners;
the plurality of loops comprising a first set of loops and a second set of loops;
the plurality of fasteners being distributed along a length of the support fabric;
the plurality of fasteners being laterally mounted onto a first surface of the support fabric;
the first set of fasteners being positioned on opposing sides of the second set of fasteners;
the first set of fasteners being detachably engaged to create the first set of loops;
the second set of fasteners being detachably engaged to create the second set of loops;
the first set of loops being created by rolling of the support fabric followed by engagement of the first set of fasteners;
the first set of loops are bigger than the second set of loops;
the first set of loops being oriented normally to the length of the support fabric;
the first set of fasteners comprising a plurality of connector ends and a plurality of connection ends;
the plurality of connector ends being positioned adjacent to terminal ends of the support fabric;
the plurality of connection ends being positioned between the plurality of connector ends;
each of the plurality of connection ends and connector ends being laterally offset from each other;
each of the plurality of connector ends being detachably engaged with a corresponding connection end to form the first set of loops, wherein the corresponding connection end is from the plurality of connector ends;
the plurality of connection ends being more than one;
each of the more than one connection ends being spaced apart from each other;
the second set of fasteners comprising a plurality of connector segments and a plurality of connection segments;
a first end of the plurality of connector segments being permanently attached to a first end of the plurality of connection segments;
each of the plurality of connector segments comprising a second end, wherein the second end is positioned opposite to the first end across the plurality of connector segments;
each of the plurality of connection segments comprising a second end, wherein the second end is positioned opposite to the first end across the plurality of connection segments; and
the second end of the plurality of connector segments being detachably engaged to the second end of the plurality of connection segments to form the second set of loops.

2. The medical tubes holder device of claim 1, wherein diameters of the first set of loops being large enough to be attached around at least one of a walker, a bed railing, and IV (intravenous) pole.

3. The medical tubes holder device of claim 1, comprising:
the support fabric comprising a third end and a fourth end;
the third end being positioned opposite to the fourth end across the length of the support fabric; and
a support loop from the first set of loops being positioned adjacent to the third end.

4. The medical tubes holder device of claim 3, wherein the support loop being wrapped around at least one of a walker, an IV pole, and a bed railing.

5. The medical tubes holder device of claim 3, comprising:
an instructional tag;
the instructional tag being affixed adjacent to the third end; and
the instructional tag indicating an orientation of the support fabric.

6. The medical tubes holder device of claim 1, wherein the plurality of fasteners is hook and loop fasteners.

7. The medical tubes holder device of claim 1, wherein diameters of the second set of loops being small enough to securely hold at least one of catheter line and IV line.

8. The medical tubes holder device of claim 1, wherein the support fabric is nylon.

9. A medical tubes holder device comprising:
a support fabric;
a plurality of fasteners;
a plurality of loops;
the plurality of fasteners comprising a first set of fasteners and a second set of fasteners;
the plurality of loops comprising a first set of loops and a second set of loops;
the plurality of fasteners being laterally integrated along a length of the support fabric;
the first set of fasteners being positioned on opposing sides of the second set of fasteners;
the first set of fasteners being detachably engaged to create the first set of loops;
the second set of fasteners being detachably engaged to create the second set of loops;
the first set of loops being created by rolling of the support fabric followed by engagement of the first set of fasteners;
the first set of loops are bigger than the second set of loops;
the first set of loops being oriented normally to the length of the support fabric;
the first set of fasteners comprising a plurality of connector ends and a plurality of connection ends;
the plurality of connector ends being positioned adjacent to terminal ends of the support fabric;
the plurality of connection ends being positioned between the plurality of connector ends;
each of the plurality of connector ends and the plurality of connection ends being laterally offset from each other;
each of the plurality of connector ends being detachably engaged with a corresponding connection end to form the first set of loops, wherein the corresponding connection end is from the plurality of connector ends;
the plurality of connection ends being six;
each of the six connection ends being spaced apart from each other;
the second set of fasteners comprising a plurality of connector segments and a plurality of connection segments;
a first end of the plurality of connector segments being permanently attached to a first end of the plurality of connection segments;
each of the plurality of connector segments comprising a second end, wherein the second end is positioned opposite to the first end across the plurality of connector segments;

each of the plurality of connection segments comprising a second end, wherein the second end is positioned opposite to the first end across the plurality of connection segments;

the second end of the plurality of connector segments being detachably engaged to the second end of the plurality of connection segments to form the second set of loops;

the support fabric comprising a third end and a fourth end;

the third end being positioned opposite to the fourth end across the length of the support fabric;

a support loop from the first set of loops being positioned adjacent to the third end; and the support loop being wrapped around at least one of a walker, an IV pole, and a bed railing.

10. The medical tubes holder device of claim 9, comprising:

an instructional tag;

the instructional tag being affixed adjacent to the third end;

the instructional tag indicating an orientation of the support fabric.

11. The medical tubes holder device of claim 9, wherein the plurality of fasteners is hook and loop fasteners.

\* \* \* \* \*